(12) United States Patent
Oikawa

(10) Patent No.: US 6,411,674 B1
(45) Date of Patent: Jun. 25, 2002

(54) RADIATION TOMOGRAPHY DEVICE AND SUBJECT EXAMINATION APPARATUS USING THE SAME

(75) Inventor: Shiro Oikawa, Shiga-ken (JP)

(73) Assignee: Shimadzu Corporation, Kyoto (JP)

( * ) Notice: Subject to any disclaimer, the term of this patent is extended or adjusted under 35 U.S.C. 154(b) by 0 days.

(21) Appl. No.: 09/557,622

(22) Filed: Apr. 25, 2000

(30) Foreign Application Priority Data

May 17, 1999 (JP) ............................................ 11-135530

(51) Int. Cl.[7] .................................................. A61B 6/02
(52) U.S. Cl. ............................................ 378/21; 378/22
(58) Field of Search .................................... 378/21–27

(56) References Cited

U.S. PATENT DOCUMENTS 5,351,278 A * 9/1994 Koshishiba et al. .......... 378/22
5,388,136 A * 2/1995 Halliday et al. ............... 378/58
5,978,440 A * 11/1999 Kang et al. .................... 378/21

* cited by examiner

*Primary Examiner*—David P. Porta
(74) *Attorney, Agent, or Firm*—Kanesaka & Takeuchi

(57) ABSTRACT

In a radiation tomography device, in case a wide photographing area is required, even if a resolution capability in a depth direction of a section of a subject including an intersection of a rotation axis and a radiation irradiating axis is low, a small Laminographic angle $\alpha 1$ is set. In case a high resolution capability is required in the depth direction, even if the photographing area is narrow, a large Laminographic angle $\alpha 2$ is set. Since a balance between the resolution capability in the depth direction of the subject and the photographing area can be adjusted by varying the Laminographic angle, the photographing modes can be freely selected to thereby carry out the tomography suitable for the photographing requirement.

11 Claims, 12 Drawing Sheets

RADIATION TOMOGRAPHY DEVICE AND SUBJECT EXAMINATION APPARATUS USING THE SAME

BACKGROUND OF THE INVENTION AND RELATED ART STATEMENT

The invention relates to a non-CT type radiation tomography device for carrying out a radiation tomography for a subject or object to be examined (hereinafter referred to simply as "subject") and a subject examination apparatus using the same, especially, to a technique which can select the photographing mode as desired.

A system for examining the subject without destruction by using X-rays has a relatively long history, and there are a simple X-ray photographing system wherein X-rays are irradiated to the subject and at the same time a transmitted X-ray image is detected by an X-ray film, imaging plate or image intensifier, i.e. I.I. Tube, to thereby take an image; and an X-ray tomography system wherein an image of a specific section of the subject is taken. In regard to the latter X-ray tomography system, there is a non-CT type tomography system which has been developed from the simple X-ray photographing system prior to an X-ray CT type, not the tomography system of the X-ray CT, i.e. X-ray computerized tomography type which has been developed remarkably. FIG. 17 is a diagram showing a structure of a photographing system in a conventional non-CT type X-ray tomography (hereinafter, referred to as "X-ray tomography"). irradiating axis Xa, of an X-ray tube R in the subject M. A detecting surface Da of a sheet-type X-ray detector D for detecting a transmitted or passed x-ray image of the subject M is held perpendicular to the rotation axis ra of the subject. An X-ray fault picture image (hereinafter referred to as "fault picture image") can be obtained by integration of the transmitted X-ray picture images sequentially obtained based on detected data outputted from the sheet-type X-ray detector D as X-rays are irradiated to the subject M and the subject M is rotated. The reason why the fault picture image can be obtained by integrating the transmitted X-ray picture images is specifically explained hereunder.

As shown in FIG. 17, the subject M has a section MA parallel to the detecting surface Da of the sheet-type X-ray detector D including an intersection Ma, and a section MB parallel to the detecting surface Da of the sheet-type X-ray detector D without including the intersection Ma in the subject M. Here, as shown in FIG. 18(a), the section MA has an X-ray shielding area with an A-character shape, and as shown in FIG. 18(b), the section MB has an X-ray shielding area with a B-character shape. Therefore, in the respective transmitted X-ray picture images sequentially obtained based on the detected data outputted from the sheet-type X-ray detector D, for example, as shown in FIG. 18(c), an A-character shape image and a B-character shape image coexist. However, a position of the A-character shape image is always fixed at the center of the picture image, and a position of the B-character shape is moved in a clockwise direction around the A-character shape image as the subject M is rotated. As a result, as shown in FIG. 18(d), in an integrated picture image of all the transmitted X-ray picture images, although the A-character shape image becomes clear due to overlapping of all the images, the B-character shape images become unclear, obscure, by being scattered in all directions. Thus, the picture image of FIG. 18(d) becomes an X-ray fault picture image emphasizing the section MA.

As described above, the non-CT type X-ray tomography system has almost the same structure as that of the simple X-ray photographing system to photograph a specific section in the subject M, so that a fault picture image can be obtained.

However, in the above conventional X-ray tomography system, it has been difficult to set an accurate photographing mode according to a photographing state. According to an object for photographing, a subject or a state of the subject M, even if an emphasizing degree of the section MA is weak, i.e. a resolving power or resolution ability in a depth direction of the fault picture image is low, there may be a case where a photographing mode having a wide photographing area is desired; or even if a photographing area is narrow, there may be a case where a photographing mode having a strong emphasizing degree, i.e. a high resolving power in a depth direction of the fault picture image, of the section MA is desired. However, in the conventional X-ray tomography system, since the range of the photographing mode which can be set is very narrow, it is difficult to set a suitable photographing mode according to a photographing condition.

In view of the above defects, the present invention has been made, and an object of the invention is to provide a radiation tomography device having various photographing modes capable of freely setting a suitable photographing mode according to a photographing situation, and a subject examination apparatus using the same.

Further objects and advantages of the invention will be apparent from the following description of the invention.

SUMMARY OF THE INVENTION

In order to attain the above objects, according to a first aspect of the invention, a radiation tomography device comprises an irradiation device for irradiating radiations to a subject; a radiation detector for detecting a transmitted or passed radiation image of the subject; a subject holding and rotating device for rotating the subject around a rotation axis intersecting a radiation irradiating axis in the subject; a Laminographic angle variation device for varying an angle, i.e. Laminographic angle, formed by the radiation irradiating axis and the rotation axis; a picture image processing device for obtaining a radiation fault picture image by storing and calculating the transmitted or passed radiation picture images sequentially obtained based on detected data outputted from the radiation detector as the radiations are irradiated to the subject by the irradiation device and the subject is rotated by the subject holding and rotating device; and a picture image display device for displaying a fault picture image obtained by the picture image processing device.

According to a second aspect of the invention, in the radiation tomography device of the first aspect, the Laminographic angle variation device is structured such that the Laminographic angle is varied by changing an inclination angle of the radiation irradiating axis with respect to the rotation axis of the subject.

According to a third aspect of the invention, in the radiation tomography device of the first aspect, the Laminographic angle variable device is structured such that the Laminographic angle is varied by changing an inclination angle of the rotation axis of the subject with respect to the radiation irradiating axis.

According to a fourth aspect of the invention, the radiation tomography device of the first aspect includes a posture holding device for holding the detecting surface of the radiation detector perpendicular to the rotation axis of the subject.

According to a fifth aspect of the invention, the radiation tomography device of the fourth aspect includes a synchronous rotation device for rotating the detecting surface in synchronism with rotation of the subject around an axis perpendicular to the detecting surface and passing through an intersection of the radiation irradiating axis and the detecting surface, in a state where the detecting surface of the radiation detector is held perpendicular to the rotation axis of the subject.

According to a sixth aspect of the invention, the radiation tomography device of any one of the first to fifth aspects includes a position changing device for changing a position of the subject with respect to the intersection of the radiation irradiating axis and the rotation axis.

According to a seventh aspect of the invention, the radiation tomography device of any one of the first to sixth aspects includes a distance varying device for varying a distance between the subject and the radiation irradiating device in a direction of the radiation irradiating axis and/or a distance between the subject and the radiation detector.

In an eighth aspect of the invention, a subject examination apparatus comprises a subject transferring device sequentially transferring subjects along a predetermined transferring route; an irradiating device for irradiating radiations to the subject transferred by the subject transferring device; a radiation detector for detecting a transmitted or passed radiation picture image of the subject; a subject rotating device for rotating the subject around a rotation axis intersecting the radiation irradiating axis in the subject; a posture holding device for holding the detecting surface of the radiation detector perpendicular to the rotation axis of the subject; a Laminographic angle variation device for varying an angle, i.e. Laminographic angle, formed by the radiation irradiating axis and the rotation axis; a picture image processing device for obtaining a fault picture image by storing and calculating transmitted or passed radiation picture images sequentially obtained based on detected data outputted from the radiation detector as radiations are irradiated by the irradiating device and the subject is rotated by the subject rotating device; and a picture image display device for displaying the radiation fault picture image obtained by the picture image processing device.

According to a ninth aspect of the invention, the subject examination apparatus of the eighth aspect is structured such that the irradiating device and the radiation detector are separately disposed above and under the transferring route of the subject.

According to a tenth aspect of the invention, the subject examination apparatus of the eighth or ninth aspect is structured such that the subject rotating device, the irradiating device and the radiation detector are disposed on a way of the subject transferring device. When the subject is transferred to a position of the subject rotating device, transfer of the subject is once stopped to rotate the subject, and at the same time, the irradiation is carried out by the irradiating device and the transmitted radiation picture images are detected by the radiation detector.

Next, operation when the radiation fault picture image is obtained by the device according to the invention, is explained.

In the tomography by the device according to the invention, the subject is rotated around the rotation axis intersecting the radiation irradiating axis of the irradiating device in the subject. Further, by storing and calculating the transmitted or passed radiation picture images in the picture image processing device, sequentially obtained based on the detected data outputted from the radiation detector as the subject is rotated and X-rays are irradiated to the subject, there is formed a fault picture image emphasizing a section, i.e. section of a portion to be photographed, parallel to the detecting surface of the radiation detector including the intersection of the radiation irradiating axis and the rotation axis, and the fault picture image is displayed on the image display device.

According to the device of the present invention, since a balance between the emphasizing degree of the section of the subject and the photographing area can be adjusted by varying the Laminographic angle through the Laminographic angle variable device, the photographing modes corresponding to the photographing situations can be freely set.

In the device according to the second aspect of the invention, the Laminographic angle is changed by the Laminographic angle variation device to correspond to a changed portion of an inclination angle of the radiation irradiating axis with respect to the rotation axis of the subject.

In the device according to the third aspect of the invention, the Laminographic angle is changed by the Laminographic angle variation device to correspond to a changed portion of an inclination angle of the rotation axis of the subject with respect to the radiation irradiating axis.

In the device according to the fourth aspect of the invention, since the detecting surface of the radiation detector is held perpendicular to the rotating axis of the subject by the posture holding device, in case a fault picture image of a section parallel to the detecting surface of the radiation detector is obtained, a load of operational process is reduced.

In the device according to the fifth aspect of the invention, the detecting surface is rotated in synchronism with rotation of the subject around an axis perpendicular to the detecting surface and passing through an intersection where the radiation irradiating axis crosses the detecting surface in a state where the detecting surface of the radiation detector is held perpendicularly by the synchronous rotation device. As a result, since a direction of the detecting surface of the radiation detector and a direction of the subject are unchangeable, when the storage and calculation of transmitted radiation picture images are carried out, a process for arranging the directions of the images is not required. In case the direction of the detecting surface of the radiation detector and the direction of the subject are changed, when the storage and calculation of the transmitted radiation picture images are carried out, the process for arranging the directions of the picture images is required.

In the device of the sixth aspect of the invention, as a position of the subject is changed with respect to the intersection of the radiation irradiating axis and the rotating axis, since a section including the intersection is changed, the section of the subject is also changed.

In the device of the seventh aspect of the invention, as a distance between the subject and the irradiating device in a direction of the radiation irradiating axis and/or a distance between the subject and the radiation detector is changed by a distance varying device, the size of the transmitted radiation picture image projected on the detecting surface is changed to thereby change the magnitude of the transmitted radiation picture image, so that a magnification of the final fault picture image is changed.

In the subject examining apparatus of the eighth aspect of the invention, a suitable Laminographic angle is set with respect to each of the subjects sequentially transferred along the predetermined transferring route by the subject transferring device, and an accurate radiation fault picture image can be obtained by taking a tomography of each of the subjects with a photographing mode suitable for a situation by adjusting a balance between the resolution capability in a depth direction of the fault picture image of the subject and the photographing area thereof.

In the apparatus of the ninth aspect of the invention, since the radiation irradiating device and the radiation detector are separately disposed above and under the transferring route of the subject, dimension in a widthwise direction of the apparatus can be reduced when compared with a case where the radiation irradiating device and the radiation detector are separately disposed on both left and right sides to cross the transferring route of the subjects.

In the apparatus of the tenth aspect of the invention, when the subject is transferred to a position where the subject rotating device is disposed, the transfer of the subject is once stopped; the subject is rotated by the subject rotating device and irradiated with the radiations by the irradiating device; and the transmitted radiation picture images are quickly detected by the radiation detector to thereby automatically carry out the tomography of the subject.

DETAILED DESCRIPTION OF PREFERRED EMBODIMENTS

Figure 2:
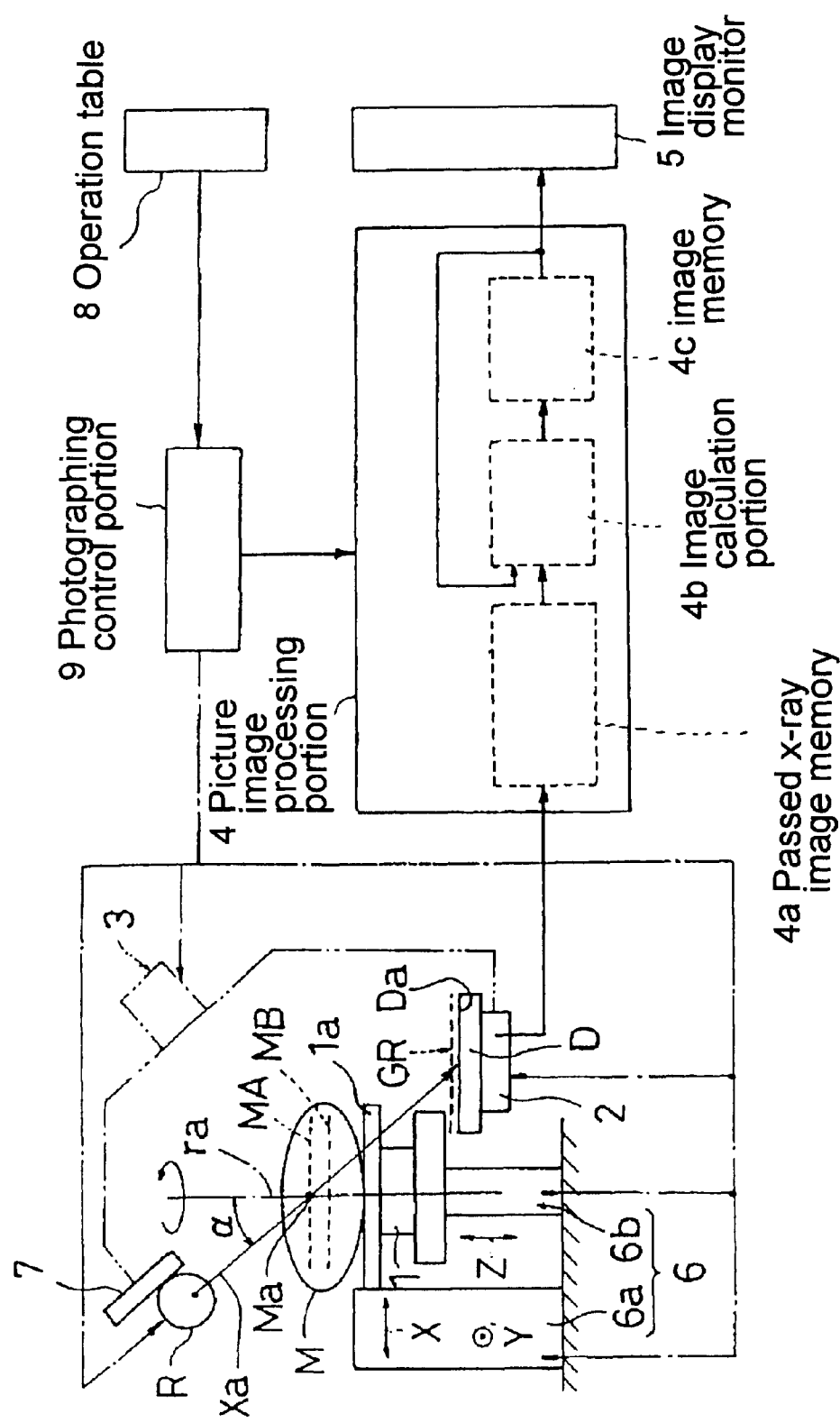
FIG. 2 is a block diagram showing the whole structure of a device according to a first embodiment.
Figure 3:
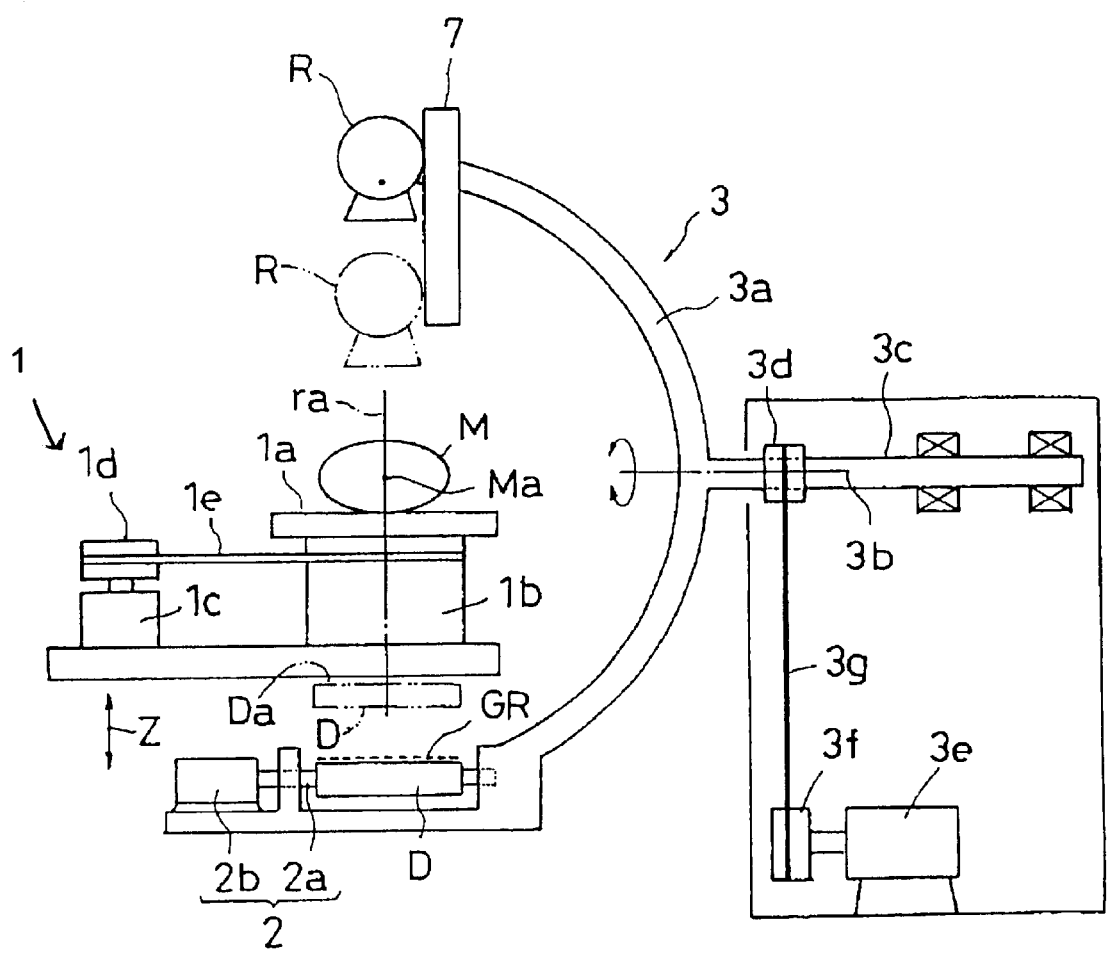
FIG. 3 is a diagram showing an essential structure of a photographing system in the device of the first embodiment.

Hereunder, embodiments of an X-ray tomography device according to the present invention are explained with reference to the accompanying drawings. FIG. 2 is a block diagram showing a whole structure of a non-X-ray CT type X-ray tomography device of a first embodiment; and FIG. 3 is a diagram showing an essential structure of an image-taking system in the device of the first embodiment.

As shown in FIG. 2, the image-taking system of the device in the first embodiment includes an X-ray tube R for irradiating X-rays to a subject M; a sheet type X-ray detector, i.e. X-ray surface sensor, D for detecting a transmitted or passed X-ray image of the subject M; a subject rotating portion 1 for rotating the subject M around a rotation axis ra, which has an intersection Ma with an X-ray irradiation axis Xa in the subject M; an examination surface posture holding portion or posture holding portion 2 for holding a detecting surface Da of the sheet-type X-ray detector D perpendicular to the rotation axis ra of the subject M; and a Laminographic angle variable or variation portion 3 for varying the Laminographic angle α, i.e. angle formed by the X-ray irradiation axis Xa and the rotation axis ra. Also, a slant grid GR for removing scattered X-rays is integrally attached in front of a detecting surface Da of the X-ray detector D.

On the other hand, a controlling system of the device in the first embodiment includes a picture image processing portion 4 for storing and operating, i.e. calculating, the transmitted or passed X-ray images; and an image display monitor 5 for displaying a fault image.

In case a tomography is carried out by the device of the first embodiment, the tomography is started after the Laminographic angle a is suitably set beforehand by the Laminographic angle variable portion 3. Thus, in the picture image processing portion 4, an X-ray fault picture image is formed through storage and calculation of the transmitted X-ray picture images sequentially obtained based on the detected data outputted from the sheet-type X-ray detector D as X-rays are irradiated to the subject M and the subject M is rotated to thereby project the fault picture image on a screen of the picture image display monitor 5.

Figure 1A:
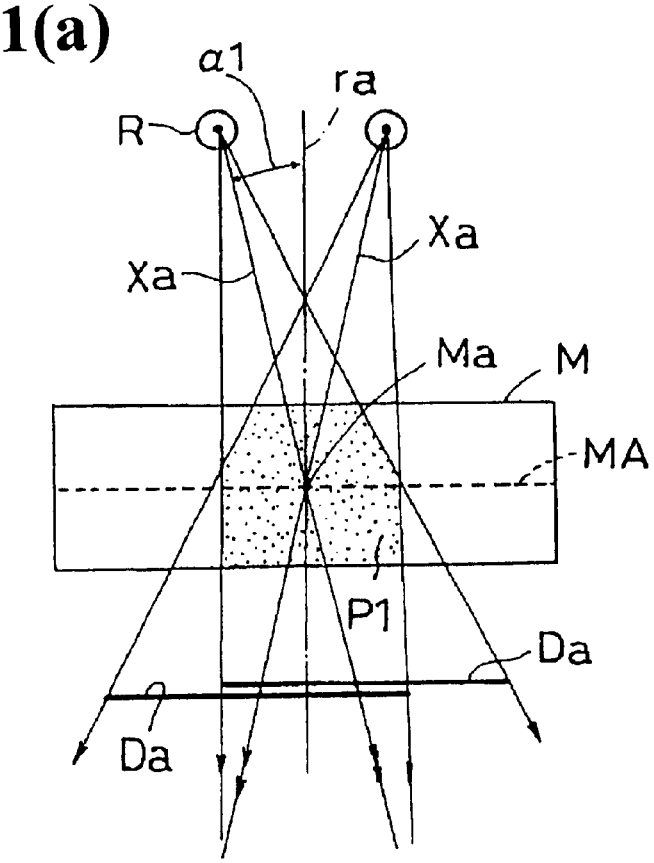
FIGS. 1(a) and 1(b) are diagrams showing set states of Laminographic angles of an X-ray tomography device according to the present invention.
Figure 1B:
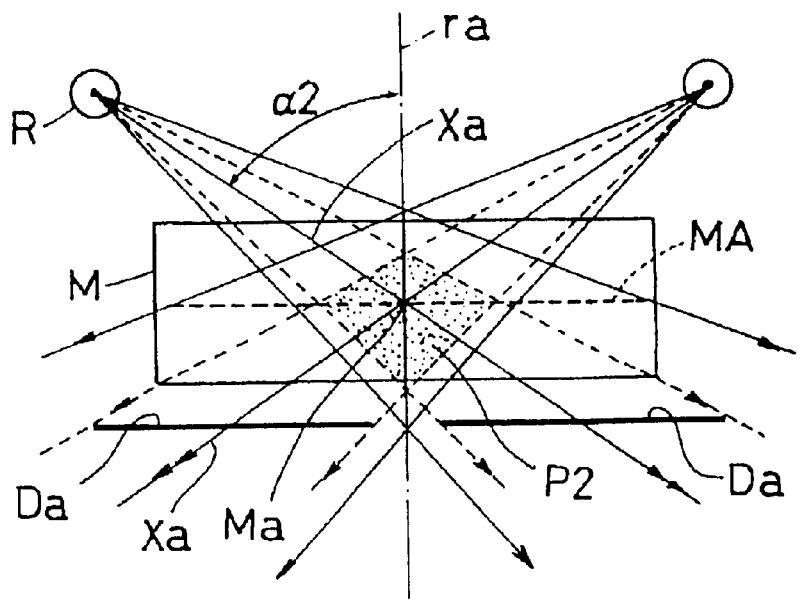

In the device according to the present invention, as shown in FIGS. 1(a) and 1(b), an angle, i.e. the Laminographic angle α, formed by the radiation irradiating axis Xa and the rotating axis ra of the subject M is set corresponding to a photographing state before the photographing starts by the Laminographic angle variation device. More specifically, in the photographing state, in case a photographing mode for covering a wide photographing area is desired even if the emphasizing degree of a section MA of the subject including the intersection Ma of the radiation irradiating axis Xa and the rotation axis ra is weak, i.e. a resolution capability in the depth direction is low, as shown in FIG. 1(a), a smaller Laminographic angle α1 is set; and in case a photographing mode having a strong emphasis on the section MA of the subject is desired even if the photographing area is narrow, as shown in FIG. 1(b), a larger Laminographic angle α2 is set.

In case the smaller Laminographic angle al is set, as shown by a dotted-area in FIG. 1(a), although the photographing area P1 where data is continuously detected during the photographing by the detecting surface Da of the radiation detector is wide, since data other than the section MA of the subject is increased, the emphasizing degree on the section MA becomes weak, i.e. the resolving power in the depth direction becomes low. In case the larger Laminographic angle α2 is set, as shown by a dotted-area in FIG. 1(b), although the photographing area P2 where data is continuously detected during the photographing by the detecting surface Da of the radiation detector is narrow, since data other than the section MA of the subject is decreased, the emphasizing degree on the section MA becomes strong, i.e. the resolution AS capability in the depth direction is increased.

Hereunder, the respective structures of the device of the first embodiment are specifically explained.

As shown in FIG. 3, the subject rotating portion 1 includes a table 1a for receiving the subject M thereon; a pulley 1b integrally attached to a lower side of the table 1a; an electric motor 1c; a pulley 1d integrally attached to the electric motor 1c; and an endless belt 1e extending between both pulleys 1b and 1d. The subject rotating portion 1 is structured such that when rotation of the electric motor 1c is transmitted to the table 1a through the pulleys 1b, 1d and the endless belt 1e, the table 1a and the subject M on the table 1a are rotated around the rotating axis ra. Incidentally, the table 1a and the pulley 1b are made of a synthetic resin having a good x-ray transmission not to cause an obstacle to the photographing.

As shown in FIG. 3, the Laminographic angle variation portion 3 includes a C-character shape arm 3a having the X-ray tube R and the sheet-type X-ray detector D on both ends, respectively; a supporting rod 3c for rotatably supporting the C-character shape arm 3a around a rotating axis 3b; a pulley 3d coaxially fixed to the supporting rod 3c; an electric motor 3e; a pulley 3f integrally attached to the electric motor 3e; and an endless belt 3g extending between both pulleys 3d, 3f. The Laminographic angle variation portion 3 is structured such that in case rotation of the electric motor 3e is transmitted to the supporting rod 3c through the pulleys 3d, 3f and the endless belt 3g to rotate the supporting rod 3c, the C-character shape arm 3a is rotated around the rotating axis 3b, so that an inclination, i.e. the Laminographic angle, of the X-ray irradiation axis Xa of the X-ray tube R with respect to the rotating axis ra is changed.

Figure 4:
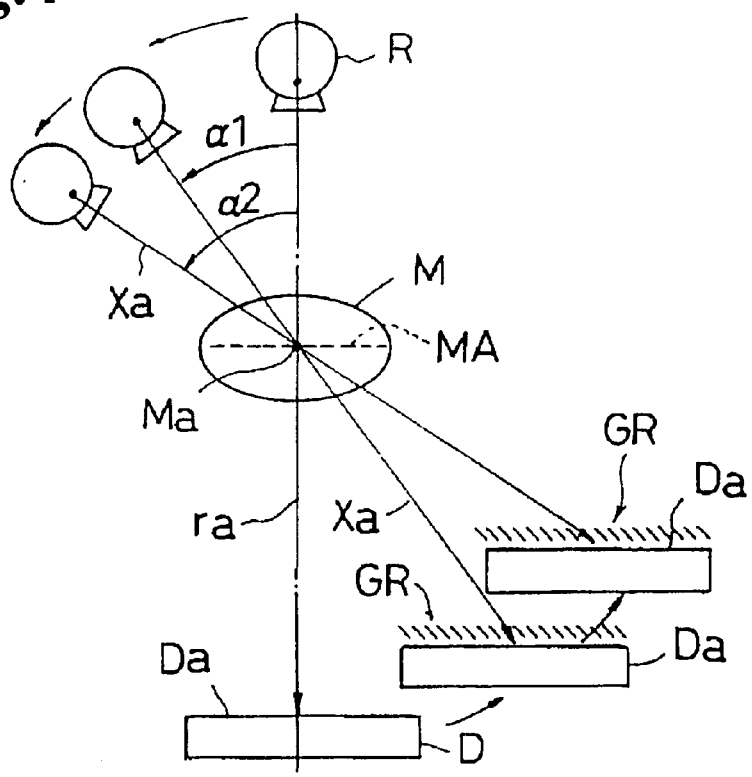
FIG. 4 is a diagram showing variable states of the Laminographic angles in the device of the first embodiment.

The Laminographic angle α in the Laminographic angle variable portion 3 is changed corresponding to a rotating quantity of the C-character shape arm 3a. More specifically, as shown in FIG. 4, in case the X-ray irradiation axis Xa of the X-ray tube R accords the rotating axis ra, the Laminographic angle α=0°; in case the C-character shape arm 3a is slightly rotated and the X-ray irradiation axis Xa is inclined with respect to the rotating axis ra, the Laminographic angle α=α1; and in case the C-character shape arm 3a is further rotated in the same direction, the inclination of the X-ray irradiation axis Xa is increased with respect to the rotating axis ra, so that the Laminographic angle α is increased to α2. It has been already mentioned that a balance between a resolving power or resolution capability in a depth direction of a fault picture image of the subject and a photographing area can be adjusted through the change of the Laminographic angle a in the Laminographic angle variable portion 3. However, in case the Laminographic angle is 0°, since the resolving power in the depth direction can not be obtained, this case can not be used in the tomography.

Figure 5:
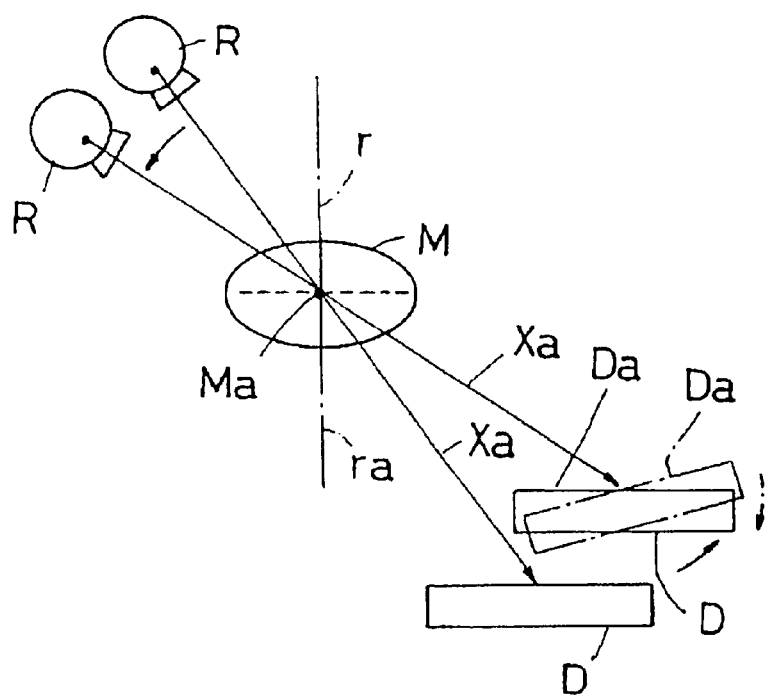
FIG. 5 is a diagram showing an inclined state of a detecting surface at the variation time of the Laminographic angle in the device of the first embodiment.

Incidentally, as shown by a single-dotted chain line in FIG. 5, in case the C-character shape arm 3a has been rotated, the detecting surface Da of the X-ray detector D can not be held in an orthogonal state with respect to the rotating axis ra of the subject M to thereby take an inclined posture. In case a fault picture image of a section parallel to the detecting surface Da is taken, if the detecting surface Da is held perpendicular to the rotating axis ra, a work load of an operation processing for obtaining the fault picture image is relieved or reduced. Therefore, in the present embodiment, the detecting surface Da of the sheet-type X-ray detector D is corrected from the inclined posture to the orthogonal posture with respect to the rotating axis ra of the subject M by the posture holding portion 2.

More specifically, as shown in FIG. 3, the detecting surface posture holding portion 2 includes an electric motor 2b and a rotating axis 2a for rotatably supporting the sheet-type X-ray detector D to change an angle of the detecting surface Da of the sheet-type X-ray detector D with respect to the rotating axis ra. Therefore, in case the C-character shape arm 3a is rotated to allow the detecting surface Da to be inclined, the electric motor 2b rotates the rotating axis 2a for a quantity corresponding to a rotating quantity of the C-character shape arm 3a to thereby always hold the detecting surface Da in the orthogonal state with respect to the rotating axis ra.

Also, the device in the first embodiment includes a position changing portion 6 for changing a position of the subject M with respect to the intersection Ma of the X-ray irradiation axis Xa and the rotating axis ra. As shown in FIG. 2, the position changing portion 6 includes a horizontal moving mechanism 6a for moving only the table 1a for receiving the subject M thereon in an X direction and in a Y direction, without moving the subject rotating portion 1, i.e. independent of the subject rotating portion 1; and a vertical moving mechanism 6b for moving the table 1a together with the subject rotating portion 1 in a Z direction to thereby change the position of the subject M with respect to the intersection Ma. In case the position of the subject M is changed with respect to the intersection Ma, since the section of the subject M including the intersection Ma is also changed, a section to be photographed is changed. In other words, the photographing position can be changed by the position changing portion 6.

Figure 6:
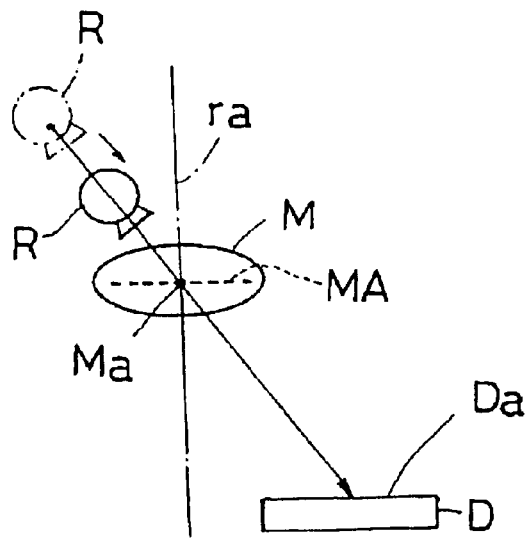
FIG. 6 is a diagram showing a state of a camera system at the variation time of the picture image magnification in the device of the first embodiment.

Further, as shown in FIGS. 3 and 6, the device in the first embodiment includes a distance variable or varying portion 7 for varying a ratio between a distance from the X-ray tube R to the subject M and a distance from the subject M to the sheet-type X-ray detector D by sliding the X-ray rube R along the X-irradiation axis Xa. In the present embodiment, although the X-ray tube R is moved, the sheet-type X-ray detector D may be moved, or both the X-ray tube R and sheet-type X-ray detector D may be moved. As a ratio between the distance from the X-ray tube R to the subject M and the distance from the subject M to the sheet-type X-ray detector D is varied by the distance variable portion 7, a size of a transmitted X-ray image projected on the detecting surface Da is changed to thereby change a magnification of a transmitted X-ray picture image, i.e. a magnification of an X-ray fault picture image. In other words, since the size of the transmitted X-ray image projected on the detecting surface Da is determined according to the ratio between the distance from the X-ray tube R to the subject M and the distance from the subject M to the sheet-type X-ray detector D, the distance variable portion 7 exhibits a picture image magnification variable function.

Also, a control for operating the respective portions on a side of a photographing system, such as the X-ray tube R, subject rotating portion 1, posture holding portion 2, Laminographic angle variable portion 3, position changing portion 6 and distance variable portion 7, is carried out by an operation table 8 and a photographing control portion 9 provided at the control side. In case the respective portions on the side of the photographing system of the device in the first embodiment are operated, it is structured such that as the necessary input operations from the operating table 8 are carried out, instruction signals corresponding to the input operations are sent from the photographing control portion 9 to the respective portions on the side of the photographing system to thereby start the operation thereof. of course, the operations of the X-ray tube R and the subject rotating portion 1 are carried out upon start of the photographing, and operations of the posture holding portion 2, Laminographic angle variable portion 3, position changing portion 6 and distance variable portion 7 are carried out before the photographing starts.

On the other hand, as shown in FIG. 2, the picture image processing portion 4 of the control system of the device in the first embodiment includes a transmitted or passed X-ray picture image memory 4a for storing detected data as the transmitted X-ray picture image outputted from the sheet-type X-ray detector D as X-rays are irradiated to the subject M and the subject M is rotated around the rotating axis ra; a picture image calculation or operating portion 4b for storing and calculating sequentially obtained transmitted X-ray picture images; and a picture image memory 4c for storing a fault picture image obtained through the storage and calculation. The picture image obtained through the storage and calculation of all the transmitted X-ray picture images obtained during one rotation of the subject M is finally stored in the picture image memory 4c as the X-ray fault picture image, and at the same time, the fault picture image is projected on a screen of a display monitor 5.

As the sheet-type X-ray detector D used in the device of the first embodiment, there can be mentioned an image intensifier and an X-ray surface sensor, i.e. flat panel type X-ray sensor, wherein a plurality of semiconductor-type X-ray detecting elements is arranged lengthwise and breadthwise. The detected data outputted from the sheet-type X-ray detector D may be a digital signal or analog signal. In case the detected data is the analog signal, it is digitized at a stage prior to transmit to the transmitted X-ray picture image memory 4a.

A process for forming the fault picture image through a picture image integration in the picture image processing portion 4 of the device in the first embodiment is not specially different from a conventional process. However, in case a direction of the detecting surface Da of the sheet-type X-ray detector D and a direction of the subject M are changed as the subject M is rotated, when the storage and calculation of the transmitted X-ray picture image are carried out at the picture image operating portion 4b, the directions of the picture images are aligned in advance.

Figure 7A:
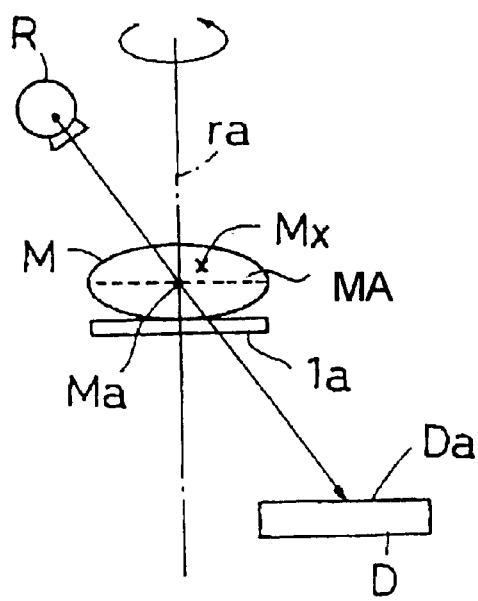
FIGS. 7(a) and 7(b) are diagrams showing states of a camera system during tomography by the device of the first embodiment.
Figure 7B:
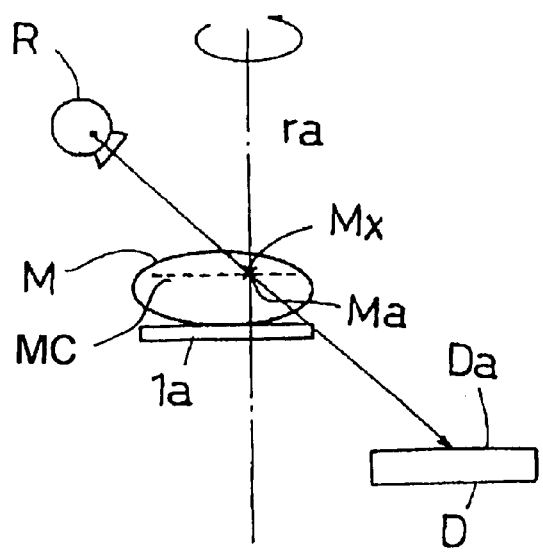
Figure 8:
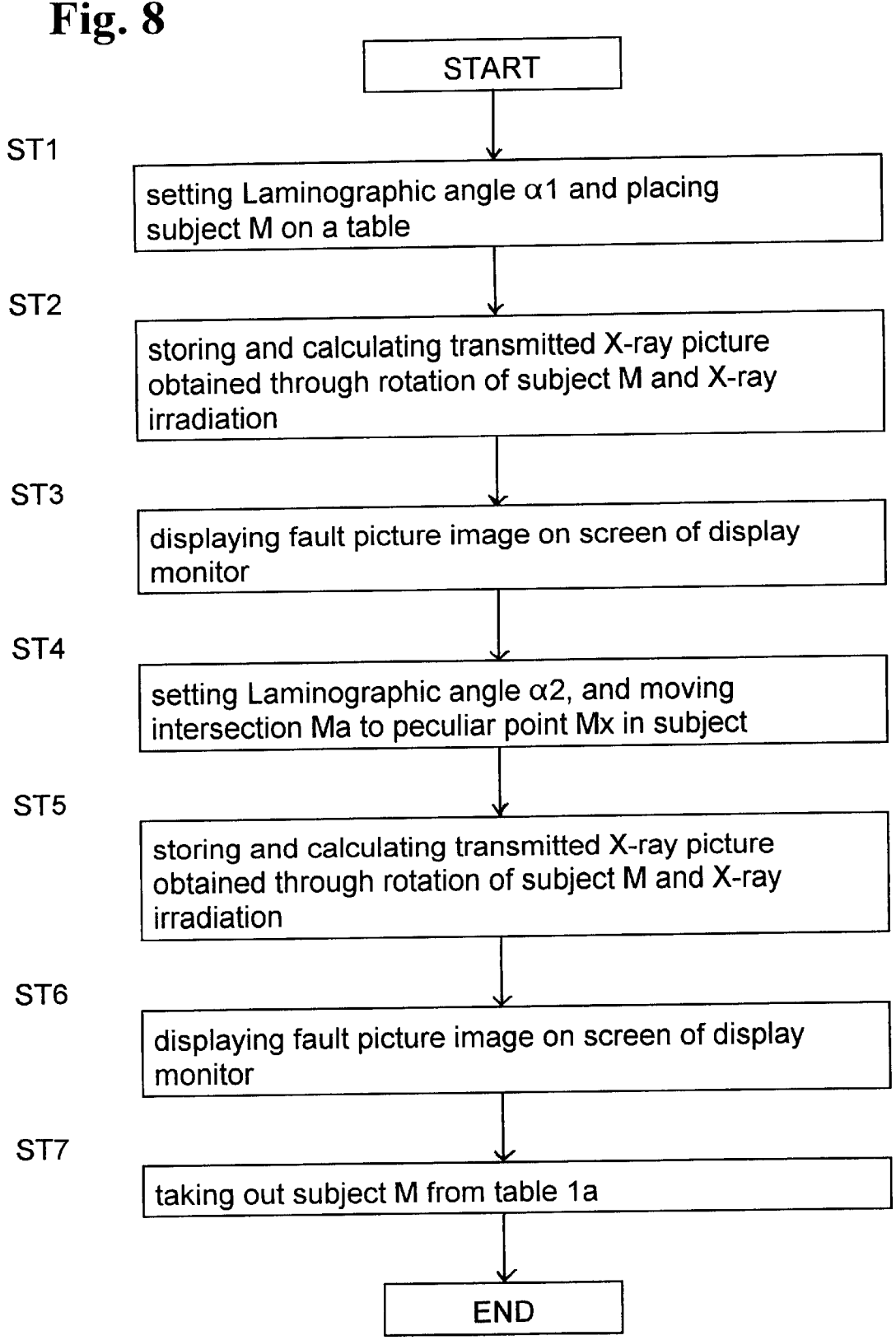
FIG. 8 is a flow chart showing states of the X-ray tomography by the first embodiment with lapse of time.

Next, an example of tomography by the X-ray tomography device in the first embodiment having the structure as described above is explained specifically with reference to the drawings. FIGS. 7(a) and 7(b) are drawings showing an essential structure of the photographing system where the photographing is being carried out by the device of the first embodiment, respectively; and FIG. 8 is a flow chart showing the states of the X-ray tomography by the device of the first embodiment with lapse of time.

Step ST1: As shown in FIG. 7(a), the photographing system is set to the narrow Laminographic angle α1, and at the same time, the subject M is placed on the table 1a so that a central point of the subject M coincides with the intersection Ma of the X-ray irradiation axis Xa and the rotation axis ra.

Step ST2: By an operation of the start of photographing, the subject M is rotated around the rotating axis ra, and X-rays are irradiated to the subject M to thereby obtain transmitted or passed X-ray picture images and to be stored and calculated.

Step ST3: When the subject M is rotated once, a fault picture image of a section MA is projected on a screen of the display monitor 5. Since the Laminographic angle α1 is set narrow, the fault picture image has a lower visibility but has a wide photographing area. A peculiar point Mx was noticed, though not clear, at a position slightly off the section MA diagonally to the upper right of the intersection Ma.

Step ST4: As shown in FIG. 7(b), the photographing system is reset to a wider Laminographic angle α2, and at the same time the subject M is moved so that the peculiar point Mx coincides with the intersection Ma by the position changing portion 6. Incidentally, in this step, if necessary, the picture image magnification may be set to a higher magnification by the distance variable portion 7.

Step ST5: Upon start of photographing, the subject M is rotated around the rotating axis ra, and at the same time, X-rays are irradiated to the subject M to obtain the transmitted X-ray picture image and to store and calculate the same.

Step ST6: When the subject M is rotated once, a fault picture image of a section MC is projected on the screen of the display monitor 5. Since the Laminographic angle α2 is widely set, though the photographing area of the fault picture image is narrow, a resolving power or resolution capability in a depth direction is high to thereby notice a clear peculiar point Mx. In case a high magnification of the transmitted X-ray picture image is set at Step ST4, the peculiar point Mx is largely projected on the screen.

Step ST7: The subject M is taken from the table 1a to complete the tomography.

Figure 9:
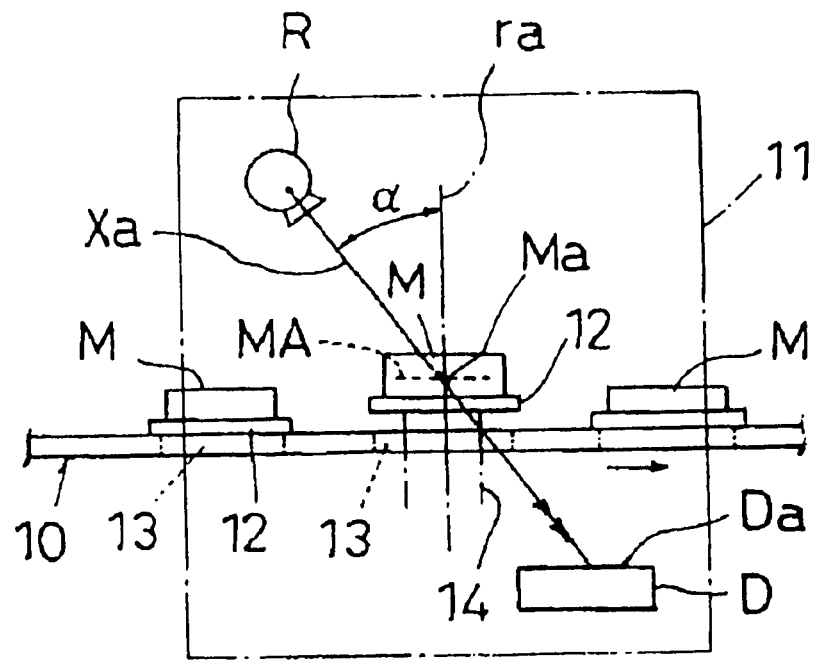
FIG. 9 is a front view of an essential part showing a state during tomography by the apparatus of a second embodiment.
Figure 10:
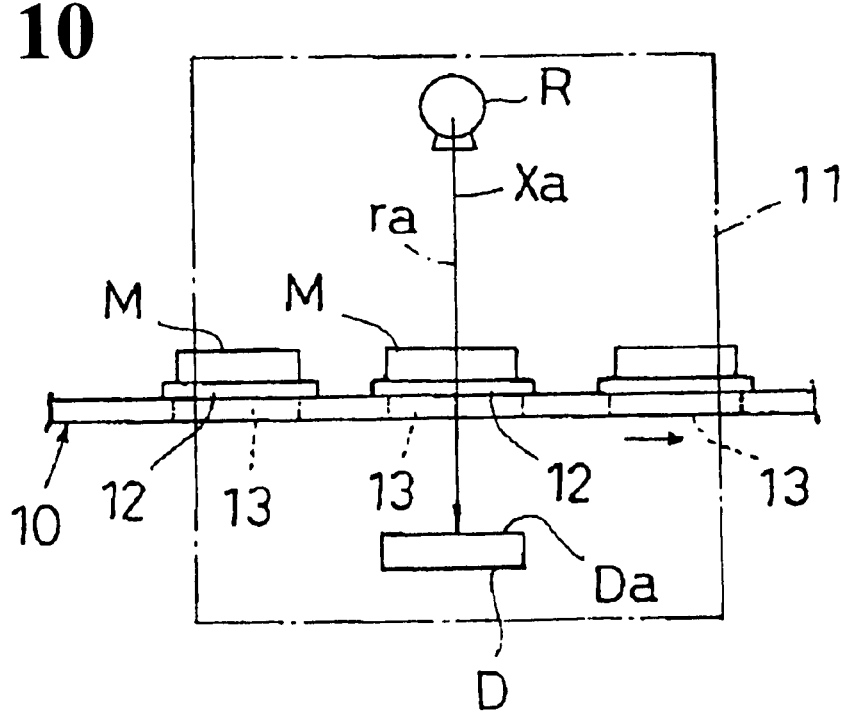
FIG. 10 is a front view of an essential part showing a state during simple X-ray photographing by the apparatus in the second embodiment.

Next, a second embodiment of a subject examination apparatus according to the present invention is explained with reference to the drawings. FIG. 9 is a front view of an essential part showing a state where a tomography is carried out by the subject examination apparatus of the second embodiment; FIG. 10 is a front view of an essential part showing a state where a simple X-ray photographing is carried out by the subject examination apparatus of the second embodiment; and FIG. 11 is a front view of an essential part showing a state where a tomography is carried out by the subject examination apparatus of the second embodiment.

Figure 11:
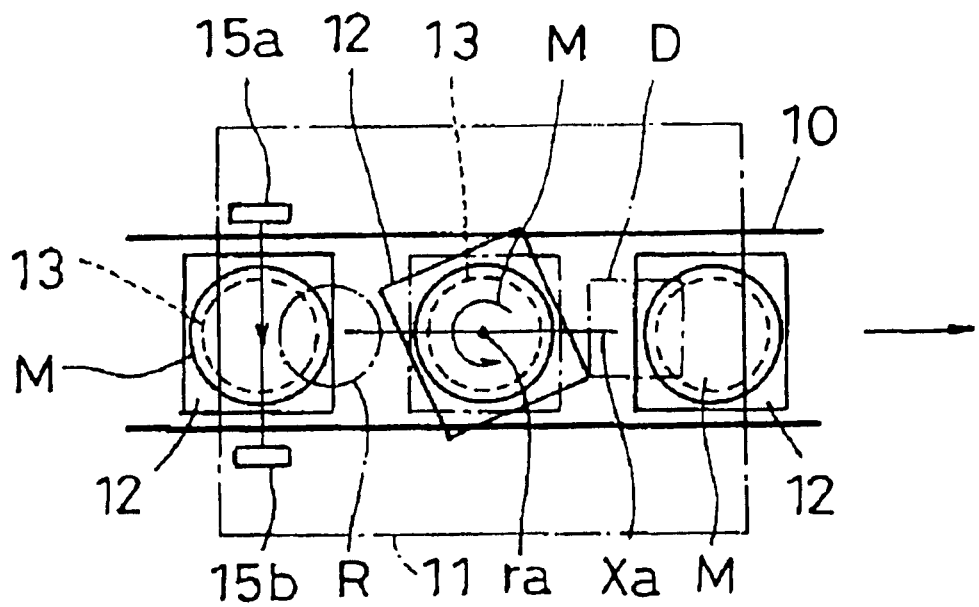
FIG. 11 is a plan view showing a state during tomography by the apparatus of the second embodiment.

As shown in FIGS. 9–11, the apparatus of the second embodiment includes a belt conveyer, i.e. subject conveying device, 10 for sequentially transferring the subjects M along a predetermined horizontal straight line, i.e. a transferring route of the subject; and an X-ray tomography portion 11 having the same structure as that of the first embodiment on the way of the horizontal straight line. The X-ray tomography is made for the transferred subject M at the X-ray tomography portion 11 to thereby examine the subject M. Hereunder, only portions different from the first embodiment are explained, and explanations for the portions common to those of the first embodiment are omitted.

In the X-ray tomography portion 11 of the apparatus of the second embodiment, since an X-ray tube R and a sheet-type X-ray detector D are separately disposed above and under the horizontal straight line for transferring the subject M, a dimension in a widthwise direction of the apparatus can be reduced when compared with a case where the X-ray tube R and the sheet-type X-ray detector D are separately disposed on the left and right sides to cross the horizontal straight line. As shown in FIG. 9, in case a tomography is carried out by the apparatus of the second embodiment, a suitable Laminographic angle α is set as in the first embodiment to take a tomography. However, as shown in FIG. 10, in case a rotating axis ra of the subject M accords an X-ray irradiation axis Xa and the Laminographic angle a is not set, i.e. α=0°, a normal simple X-ray photographing is carried out instead of the tomography, and the subject M is not rotated. In other words, in the X-ray tomography portion 11 of the apparatus in the second embodiment, not only the tomography but also the simple X-ray photographing can be selectively carried out. Of course, the Laminographic angle α is set at any angle other than 0° and the simple X-ray photographing can also be carried out from an oblique direction.

In the second embodiment, the subject M placed on a receiving plate 12 is transferred to a photographing position by the belt conveyer 10. On the other hand, a portion of the belt conveyer 10 where the receiving plate 12 is placed is provided with a big hole 13, and when the subject M reaches the photographing position, the belt conveyer 10 is once stopped and the subject M is raised together with the receiving plate 12 by a head of the subject rotating portion 14 elevated from the big hole 13. At the same time, as shown in FIG. 11, the subject M is rotated around the rotating axis ra. As in the first embodiment, an X-ray fault picture image is taken as the subject M is rotated; X-rays are irradiated; and the transmitted X-ray images are stored and calculated. Therefore, the receiving plate 12 is made of a synthetic resin, such as acrylic resin, which absorbs less X-rays. Of course, the X-ray fault picture image is projected on a screen of a display monitor to make necessary examinations.

When the tomography is completed, the subject rotating portion 14 is withdrawn from the big hole 13; the subject M is returned on the belt conveyer 10 together with the receiving plate 12; the belt conveyer 10 starts moving again; the already photographed subject M is sent out; and at the same time, another non-photographed subject M is sent to the photographing position to repeat the same procedures.

Figure 12:
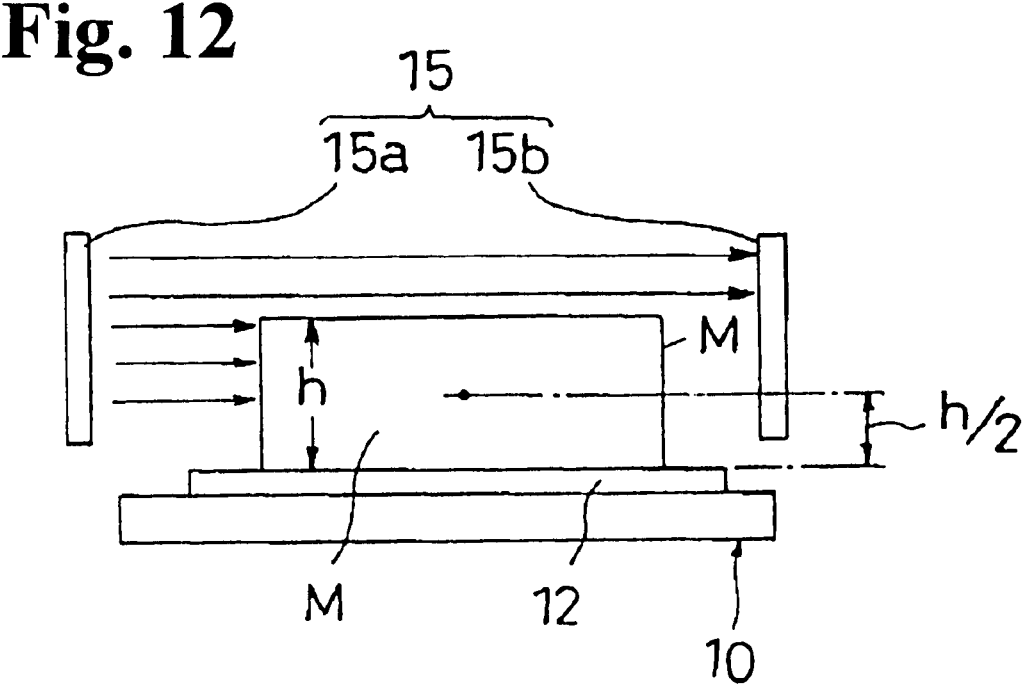
FIG. 12 is a side view for showing a height measuring portion of the apparatus in the second embodiment.

Also, in case of the apparatus of the second embodiment, as shown in FIG. 12, a height measuring portion 15 for measuring a height of the subject M is provided on both sides of the belt conveyer 10. The height measuring portion 15 includes a light projecting element alley 15a provided with a plurality of light projecting elements, for projecting lights in a horizontal direction, disposed in a vertical direction with predetermined spaces; and a light receiving element alley 15b provided with a plurality of light receiving elements and disposed in the same arrangement as that of the light projecting elements. Both light projecting element alley 15a and light receiving element alley 15b are provided to face each other on both sides of the belt conveyer 10 so that the lights from the respective light projecting elements are received by the corresponding light receiving elements.

When the subject M arrives at the height measuring portion 15, since the lights of the light projecting elements present at positions lower than the height of the subject M are blocked, the light receiving element located at the highest position among the light receiving elements which can not receive the lights is detected, and the height h of the subject M is calculated from the position of the light receiving element at the highest position. The height measuring portion 15 is used for determining a photographing section according to the size, i.e. height, of the subject M, as described later.

Figure 13:
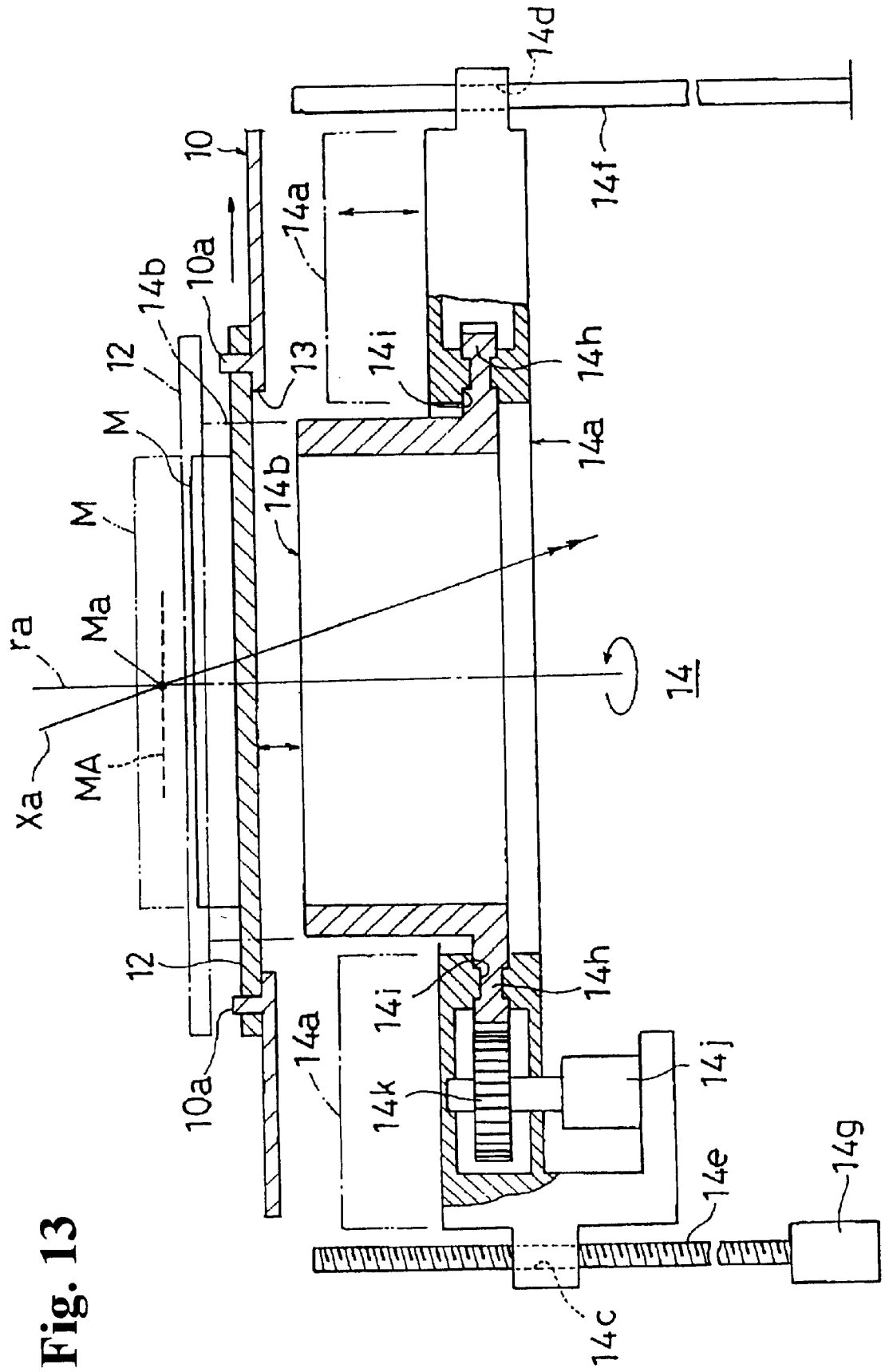
FIG. 13 is a front view showing a structure of a subject rotating portion of the apparatus in the second embodiment.

Next, a structure around the subject rotating portion 14 is specifically explained. As shown in FIG. 13, the subject rotating portion 14 includes a vertically movable supporting ring member 14a disposed right under the belt conveyer 10; and a rotating ring member 14b engaging an inside of the supporting ring member 14a to be rotatable in a peripheral direction thereof.

The supporting ring member 14a includes a screw hole 14c disposed in a vertical direction on one of opposed positions provided in the peripheral direction; and a non-screw hole 14d disposed in a vertical direction on the other position. The screw hole 14c is connected to a screw bar 14e disposed in a vertical direction, and the non-screw hole 14d is engaged with a guide bar 14f provided in the vertical direction. A lower end of the screw bar 14e is connected to a rotating shaft of an electric motor 14g, and the supporting ring member 14a is elevated or lowered as the screw bar 14e rotates according to a normal rotation or a reverse rotation of the electric motor 14g.

On the other hand, the rotating ring member 14b includes an engagement projection 14h disposed to surround a lower edge of an outer circumferential surface in a circumferential direction. The supporting ring member 14a includes an engagement indentation 14i disposed to surround a center of an inner circumferential surface in a circumferential direction. The engagement projection 14h engages the engagement indentation 14i not to move in a vertical direction but only movable in the circumferential direction. Moreover, a whole circumferential surface of the engagement projection 14h is provided with gear teeth. On the other hand, the supporting ring member 14a is provided with a rotation gear 14k engaging the engagement projection 14h and providing a power to rotate in a circumferential direction as an electric motor 14j is rotated.

As a result, as the rotation gear 14k is rotated through rotation of an electric motor 14j, power is given to the engagement projection 14h in the circumferential direction to thereby rotate the rotation ring member 14b around the rotation axis ra. Also, the supporting ring member 14a is elevated or lowered in cooperation with a vertical movement of the rotation ring member 14b.

As the supporting ring member 14a is elevated through rotation of the electric motor 14g, an upper end of the rotating ring member 14b is also elevated, as shown by a single dotted chain line in FIG. 13, to raise the receiving plate 12 while separating engagement holes 12a of the receiving plate 12 from engaging pins 10a through the big hole 13 of the belt conveyer 10. When the electric motor 14j is rotated in a state where the receiving plate 12 is elevated, the rotating ring member 14b is rotated, so that the receiving plate 12 and the subject M received thereon are rotated around the rotation axis ra.

When the subject M is rotated once, the supporting ring member 14a is lowered through reverse rotation of the electric motor 14g, and the upper end of the rotation ring member 14b is also lowered, as shown by a solid line in FIG. 13. Also, the receiving plate 12 is returned to the original state while the engagement pins 10a are being fitted into the engagement holes 12a of the receiving plate 12.

Incidentally, in the apparatus of the second embodiment, an elevating height of the upper end of the rotation ring member 14b can be controlled so that in a middle position of the height, i.e. h/2, the subject M is automatically positioned on the intersection Ma based on the height h of the subject M measured by the height measuring portion 15.

Next, subject examination by the subject examination apparatus of the second embodiment having the structure as described above is explained.

Normally, as shown in FIG. 10, a subject is examined through a simple fluoroscopy picture image by a simple X-ray photographing at Laminographic angle α=0°, and in case the subject is determined as requiring a special attention, the Laminographic angle α is set to a suitable angle, for example, α1 and, at the same time, the subject M is elevated by the subject rotating portion 14 to rotate and obtain an X-ray fault picture image through the X-ray irradiation. Since the tomography takes a longer time when compared with the simple X-ray photographing, the subject M which does not require the tomography can be examined with the simple X-ray photographing.

Incidentally, in the X-ray tomography portion 11 of the apparatus according to the second embodiment, as in the first embodiment, if the position changing portion 6 and the distance variable portion 7 are also provided, usefulness of the subject examination apparatus can be increased.

Although the apparatus according to the second embodiment can be applied to an aviation luggage inspection, a joint portion examination of an electronic component mounting board or a material surface examination of a composite material, it is needless to say that the apparatus of the second embodiment is not limited to the above-mentioned examinations.

Also, the simple X-ray photographing is carried out by a different apparatus, and only the subject M determined as requiring a special attention may be subjected to the X-ray tomography.

The present invention is not limited to the above-described embodiments, and modified embodiments as described below may be employed.

(1) In the above embodiments, although the radiations irradiated to the subject are X-rays irradiated from the X-ray tube, the radiations irradiated to the subject may be X-rays irradiated from a plasma X-ray source; X-rays irradiated from an medical linear accelerator; mono-X-rays irradiated from an SOR light source; or, further, gamma-rays or neutron-rays irradiated from a radio isotope.

Figure 14:
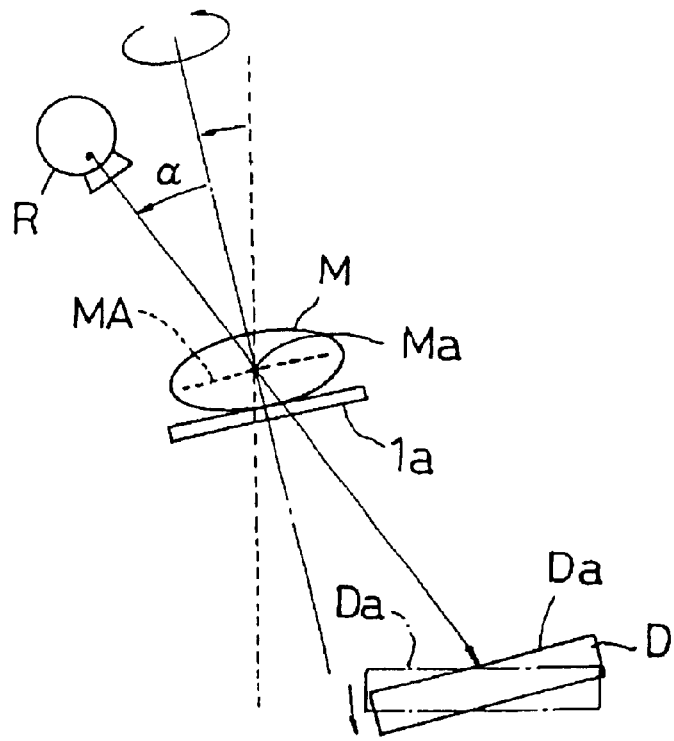
FIG. 14 is a diagram showing an essential structure of a photographing system of an apparatus in a modified example.

(2) In the above embodiments, although change of the Laminographic angle α is carried out by varying the inclination angle of the X-ray irradiation axis with respect to the rotating axis ra of the subject, a modified example may be made wherein the change of the Laminographic angle α is carried out by varying the inclination angle of the rotation axis ra of the subject M with respect to the X-ray irradiation axis Xa, as shown in FIG. 14. In the apparatus according to the modified example, in case the inclination angle of the rotation axis ra is changed, an inclined state of the detecting surface Da of the sheet-type X-ray detector D as shown by a single dotted chain line in FIG. 14 is required to be corrected to an orthogonal state as shown by a solid line in FIG. 14.

Figure 15:
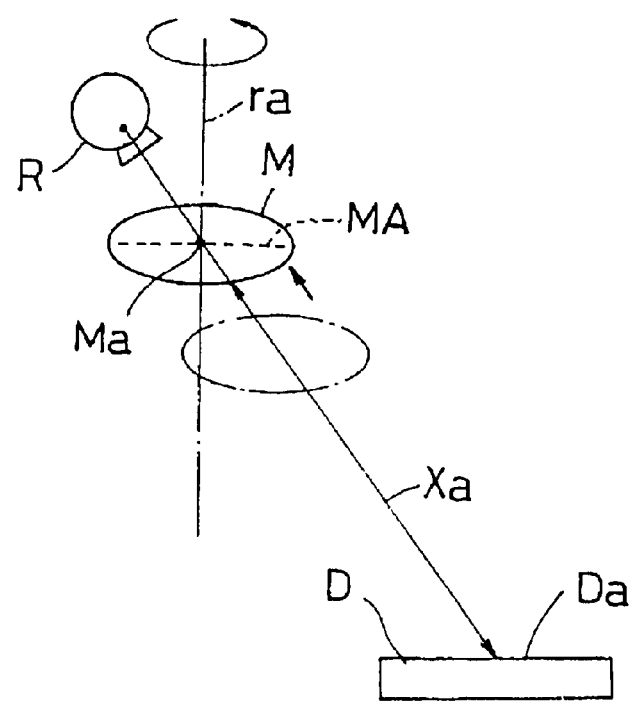
FIG. 15 is a diagram showing an essential structure of a photographing system of an apparatus in another modified example.

(3) In the above embodiments, the picture image magnification is changed by varying a ratio of a distance from the X-ray tube R to the subject M and a distance from the subject M to the sheet-type X-ray detector D by sliding the X-ray tube R along the X-ray irradiation axis Xa. However, there may be employed a structure wherein the picture image magnification is changed by varying a ratio of a distance from the X-ray tube R to the subject M and a distance from the subject M to the sheet-type X-ray detector D by sliding the subject M along the X-ray irradiation axis Xa, as shown in FIG. 15.

Figure 16:
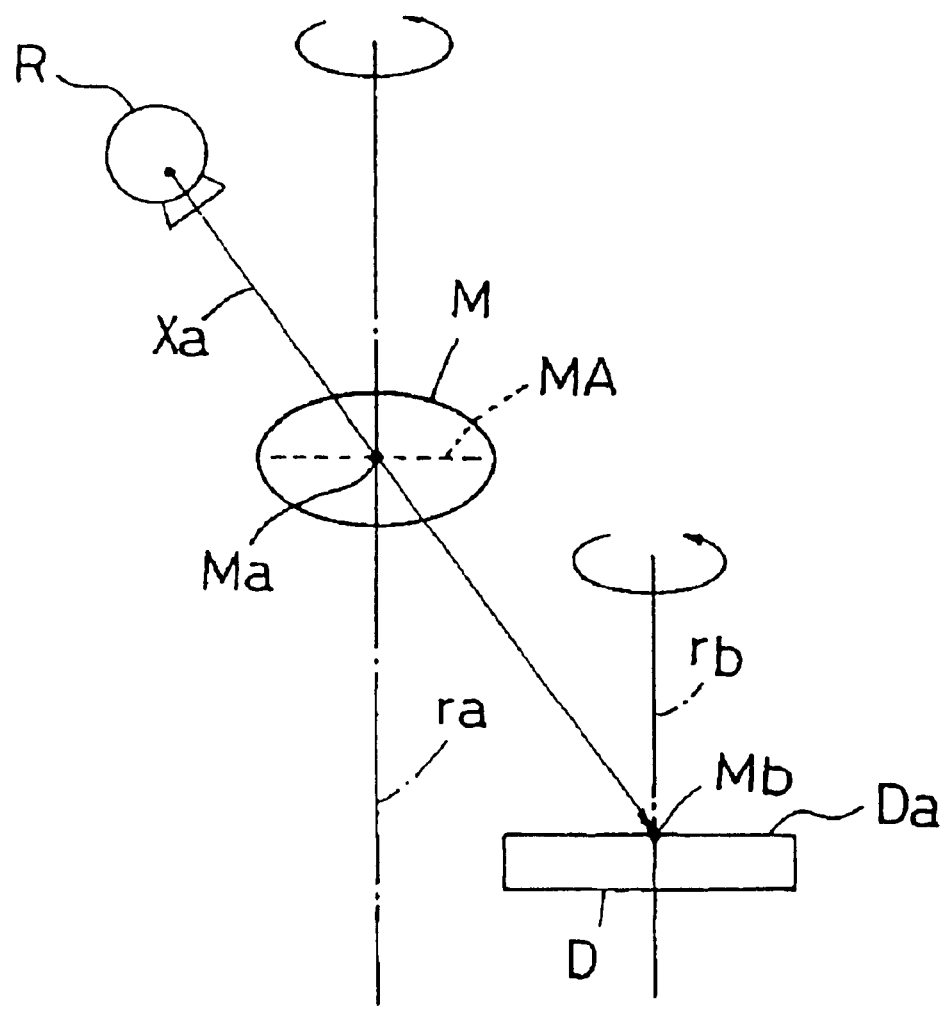
FIG. 16 is a diagram showing an essential structure of a photographing system of an apparatus in still another modified example.
Figure 17:
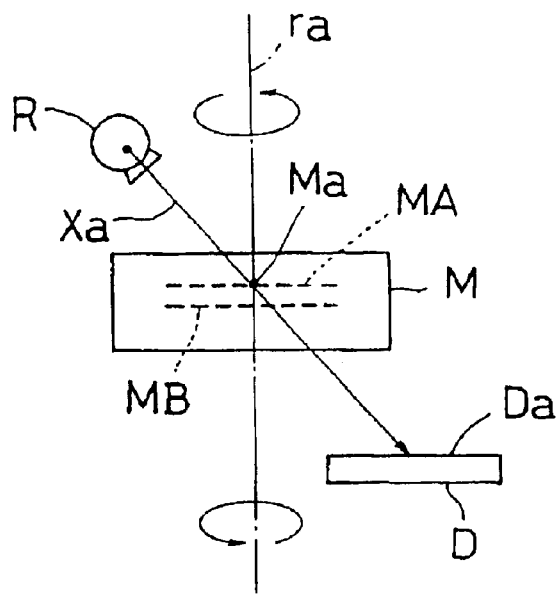
FIG. 17 is a diagram showing an essential structure of a photographing system of a conventional apparatus.
Figure 18A:
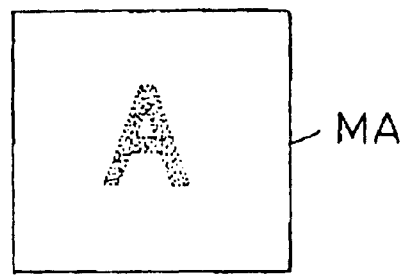
FIGS. 18(a) to 18(d) are diagrams for explaining a forming process of an X-ray tomography in the conventional apparatus.
Figure 18B:
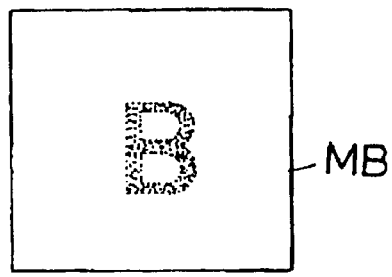
Figure 18C:
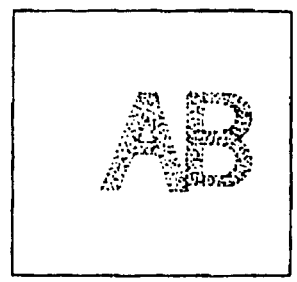
Figure 18D:
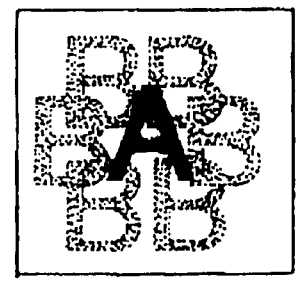

(4) In the above embodiments, during photographing, the subject M is rotated, and the sheet-type X-ray detector D is immovable. However, as shown in FIG. 16, there may be a modified example wherein in a state where the detecting surface Da of the sheet-type X-ray detector D is held perpendicular to the rotation axis ra, the X-ray irradiation axis Xa passes through the intersection Mb intersecting the detecting surface Da, so that the sheet-type X-ray detector D, i.e. detecting surface Da, is rotated in synchronism with the rotation of the subject M around the rotation axis rb perpendicular to the detecting surface Da. In the modified example, since the direction of the detecting surface Da of the sheet-type X-ray detector D and the direction of the subject M are unchangeable, the directions of the picture images are not required to be aligned when the storage and calculation of the transmitted X-ray picture images are carried out.

(5) Although the above embodiment is structured such that the detecting surface Da of the sheet-type X-ray detector D is held perpendicular to the rotating axis ra of the subject M, this invention is not always limited to the structure. For example, the detecting surface Da may be held perpendicular to the X-ray irradiation axis Xa.

As apparent from the above explanation, according to the first aspect of the radiation tomography device of the invention, the Laminographic angle is varied by the Laminographic angle variable device, and a balance between a resolution capability in the depth direction of the fault picture image of the subject and the photographing area can be adjusted. Therefore, the photographing mode can be freely varied, so that any photographing mode suitable for a situation can be set.

According to the second aspect of the radiation tomography device of the invention, a suitable Laminographic angle can be set by varying an inclination angle of the radiation irradiating axis with respect to the rotation axis of the subject.

According to the third aspect of the radiation tomography device of the invention, a suitable Laminographic angle can be set by varying an inclination angle of the rotation axis of the subject with respect to the radiation irradiating axis.

According to the fourth aspect of the radiation tomography device of the invention, since the detecting surface of the radiation detector is held perpendicular to the rotating axis of the subject, in case the fault picture image of a section parallel to the detecting surface of the radiation detector is obtained, a load in the calculation process can be reduced.

According to the fifth aspect of the radiation tomography device of the invention, since a direction of the detecting surface of the radiation detector and a direction of the subject are unchanged, at the time of storage and calculation of transmitted or passed radiation picture images, the directions of the picture images are not required to be aligned.

According to the sixth aspect of the radiation tomography device of the invention, since a sectional area including an intersection of the radiation irradiating axis and the rotation axis is varied, a section of the subject, i.e. photographing position, can be changed.

According to the seventh aspect of the radiation tomography device of the invention, by changing a distance between the subject and the radiation irradiating device, and/or a distance between the subject and the radiation detector, a magnification of the radiation fault picture image can be changed.

According to the eighth aspect of the invention, in a subject examination apparatus, a suitable Laminographic angle can be set with respect to each subject sequentially sent by a subject transferring device along a predetermined transferring route, and each subject can be subjected to a tomography in a photographing mode suitable for a situation by adjusting a balance between a resolution capability in a depth direction of the fault picture image of the subject and the photographing area. Thus, an accurate examination can be carried out based on the radiation fault picture image obtained in the mode suitable for the situation.

According to the ninth aspect, in the subject examination apparatus of the invention, since the radiation irradiating device and the radiation detector are provided separately above and below the transferring route of the subject, dimension of the apparatus in the widthwise direction can be reduced to thereby make the apparatus compact.

According to the tenth aspect, in the subject examination apparatus of the invention, when the subject is transferred to the position where the subject rotating device is disposed, the subject is rotated by the subject rotating device and irradiated with radiations by the irradiating device, and the transmitted radiation image is detected quickly by the radiation detector to thereby automatically carry out a tomography of the subject.

While the invention has been explained with reference to the specific embodiments of the invention, the explanation is illustrative and the invention is limited only by the appended claims.

What is claimed is:

1. A radiation-tomography device comprising:
    an irradiating device for irradiating radiations to a subject to be examined;
    a radiation detector situated at a predetermined distance away from the irradiating device for detecting radiation picture images passing through the subject;
    a subject holding and rotating device situated between the irradiating device and radiation detector for holding and rotating the subject around a rotating axis, which intersects in the subject an irradiating axis from the irradiating device to the subject;
    a posture holding device for holding a detecting surface of the radiation detector perpendicular to the rotating axis of the subject;
    a Laminographic angle variation device attached to at least one of the irradiating device and the subject holding and rotating device, said Laminographic angle variation device varying a Laminographic angle formed by the radiation irradiating axis and the rotating axis;
    a picture image processing device electrically connected to the radiation detector for obtaining a radiation fault picture image, said picture image processing device storing and calculating the radiation picture images sequentially obtained based on detected data outputted from the radiation detector as the subject is irradiated by the irradiating device and is rotated by the subject holding and rotating device; and
    a picture image display device for displaying the fault picture image obtained by the picture image processing device.

2. A radiation tomography device as claimed in claim 1, wherein said Laminographic angle variation device is a device for changing an inclination angle of the radiation irradiating axis with respect to the rotation axis of the subject.

3. A radiation tomography device as claimed in claim 1, wherein said Laminographic angle variation device is a device for changing an inclination angle of the rotation axis of the subject with respect to the radiation irradiating axis.

4. A radiation tomography device as claimed in claim 1, further comprising a synchronous rotation device for rotating the detecting surface in synchronism with rotation of the subject around an axis perpendicular to the detecting surface passing through an intersection between the radiation irradiating axis and the detecting surface, in a state where said detecting surface of the radiation detector is held perpendicular to the rotation axis of the subject.

5. A radiation tomography device as claimed in claim 1, further comprising a position changing device for changing a position of the subject with respect to an intersection between the rotating axis and the radiation irradiating axis.

6. A radiation tomography device as claimed in claim 1, further comprising a distance varying device for changing at least one of a distance between the subject and the radiation irradiating device in a direction of the radiation irradiating axis and a distance between the subject and the radiation detector.

7. A radiation tomography device as claimed in claim 1, wherein said Laminographic angle variation device includes an arm for holding the radiation device at one end and the radiation detector at the other end, a shaft attached to the arm, and a rotation device attached to the shaft to change an angle of the arm.

8. A subject examination apparatus comprising:
    a subject transferring device for sequentially transferring subjects to be examined along a predetermined transferring route;
    an irradiating device situated at a predetermined distance away from the subject transferring device for irradiating radiations to each of the subjects transferred by the subject transferring device;
    a radiation detector situated at a side opposite to the irradiating device relative to the subject transferring device for detecting passed radiation picture images of the subject;
    a subject holding and rotating device situated at one side of the subject transferring device for rotating the subject transferred by the subject transferring device around a rotating axis, said rotating axis crossing an irradiating axis from the irradiating device in the subject;
    a posture holding device attached to the radiation detector for holding a detecting surface of the radiation detector perpendicular to the rotation axis of the subject;
    a Laminographic angle variation device attached to the irradiation device for varying a Laminographic angle formed by the irradiating axis and the rotation axis;
    a picture image processing device attached to the radiation detector for obtaining a fault picture image, said picture image processing device storing and calculating the radiation picture images sequentially obtained based on detected data outputted from the radiation detector as the radiations are irradiated by the irradiating device and the subject is rotated by the subject holding and rotating device; and
    a picture image display device attached to the picture image processing device for displaying the fault picture image obtained by the picture image processing device.

9. A subject examination apparatus as claimed in claim 8, wherein said irradiating device and said radiation detector are disposed separately above and under the transferring route of the subject.

10. A subject examination apparatus as claimed in claim 8, wherein the subject rotating device, the irradiating device and the radiation detector are disposed on a part of the subject transferring device, and when the subject is transferred to a position where the subject holding and rotating device is disposed, the subject transferring device is stopped and the subject holding and rotating device is actuated while the irradiating device is operated to obtain the radiation picture images by the radiation detector.

11. A subject examination apparatus as claimed in claim 8, wherein said subject transferring device includes a conveyor and tables disposed on the conveyor to place the subjects thereon, said subject holding and rotating device sequentially raising one table and rotating the same.

* * * * *